US006788406B2

(12) United States Patent
Ross

(10) Patent No.: US 6,788,406 B2
(45) Date of Patent: Sep. 7, 2004

(54) DEVICE AND METHODS OF INSPECTING SOLDERED CONNECTIONS

(75) Inventor: Graham Ross, Foothill Ranch, CA (US)

(73) Assignee: Delaware Capital Formation, Inc., Wilmington, DE (US)

( * ) Notice: Subject to any disclaimer, the term of this patent is extended or adjusted under 35 U.S.C. 154(b) by 1 day.

(21) Appl. No.: 10/033,573

(22) Filed: Nov. 2, 2001

(65) Prior Publication Data

US 2003/0086084 A1 May 8, 2003

(51) Int. Cl.$^7$ ............................................. G01N 21/954
(52) U.S. Cl. ............................... 356/241.5; 356/341.4; 356/241.1
(58) Field of Search ................ 356/241.1, 241.3–241.6, 356/237.1, 237.2–237.5; 382/150; 348/661, 65, 68; 600/129, 160–165, 171, 173; 359/667

(56) References Cited

U.S. PATENT DOCUMENTS

| | | |
|---|---|---|
| 1,216,724 A | 2/1917 | Petrie |
| 1,932,470 A | 10/1933 | Lehmann |
| 4,686,565 A | 8/1987 | Ando |
| 4,699,463 A | 10/1987 | D'Amelio et al. |
| 4,727,859 A * | 3/1988 | Lia ........................... 356/241.5 |
| 4,753,224 A * | 6/1988 | Tojo ......................... 356/241.5 |
| 4,825,259 A * | 4/1989 | Berry, Jr. .................. 356/241.4 |
| 5,194,948 A | 3/1993 | L'Esperance, III et al. |
| 5,465,152 A | 11/1995 | Bilodeau et al. |
| 5,621,530 A | 4/1997 | Marrable, Jr. |
| 5,955,683 A | 9/1999 | Holliday |
| 6,043,876 A | 3/2000 | Holliday et al. |
| 6,288,346 B1 | 9/2001 | Ojiri et al. |
| 6,535,283 B1 * | 3/2003 | Heffels et al. .............. 356/300 |
| 6,580,501 B2 * | 6/2003 | Cannon .................... 356/237.1 |
| 2001/0024273 A1 | 9/2001 | Cannon |

FOREIGN PATENT DOCUMENTS

| | | |
|---|---|---|
| EP | 0634892 | 1/1995 |
| EP | 0994646 | 4/2000 |
| WO | WO 99/44409 | 9/1999 |

OTHER PUBLICATIONS

Ersa, Ersascope Inspection System 3000 International Awards, *Circuits Assembly*, 6 pages (Dec. 1999).
Ersa, *Inspection Systems*, 5 pages (1999).
Allgaier, M.W., et al., "Visual and Optical Testing", Nondestructive Testing Handbook, Oct. 2002, pp. 4, 5, 7, 14, 52, 67, 82–91, vol. 8, American Society for Nondestructive Testing.
"Section 2. Visual Inspection", Author Unknown, Publication Unknown, pp. 5–9–5–14, Sep. 8, 1998.

(List continued on next page.)

*Primary Examiner*—Richard A. Rosenberger
*Assistant Examiner*—Vincent P. Barth
(74) *Attorney, Agent, or Firm*—Burns, Doane, Swecker & Mathis, L.L.P.

(57) ABSTRACT

A device for inspecting solder connections between a component and a substrate or between two components or substrates, wherein the component is disposed upon the surface of the substrate, the device including an image receiving unit. An image transmitting device, the image transmitting device including a first end and a second end, the first end coupled to the image receiving unit. A tip assembly removably coupled to the second end of the image transmitting device, the tip assembly further including a mirror and an image receiving aperture, the tip assembly configured to transmit an image of the solder connections received by the mirror, through the image transmitting device, to the image receiving unit, and an illumination device, the illumination device including a light source, at least one light transmitting device, and at least one light emitting aperture disposed adjacent the image receiving aperture, the light emitting aperture directed towards the solder connections to be inspected.

23 Claims, 4 Drawing Sheets

OTHER PUBLICATIONS

Iddings, F.A., "Back to Basics", http://www.asnt.org/publications/materialseval/basics/jul98basics/jul98basics.htm, American Society for Nondestructive Testing.

"Storage, Use and Care of Borescopes and Fibrescopes", SAE International, pp. 1–9, Mar. 1997.

"Accessories and Attachments", http://www.provision100.com/accessory.html, Provision.

"History of Lenox Instrument Company 1900–1920", http://www.lenoxinst.com/about_history_01.shtml, Lenox Instrument Compnay.

* cited by examiner

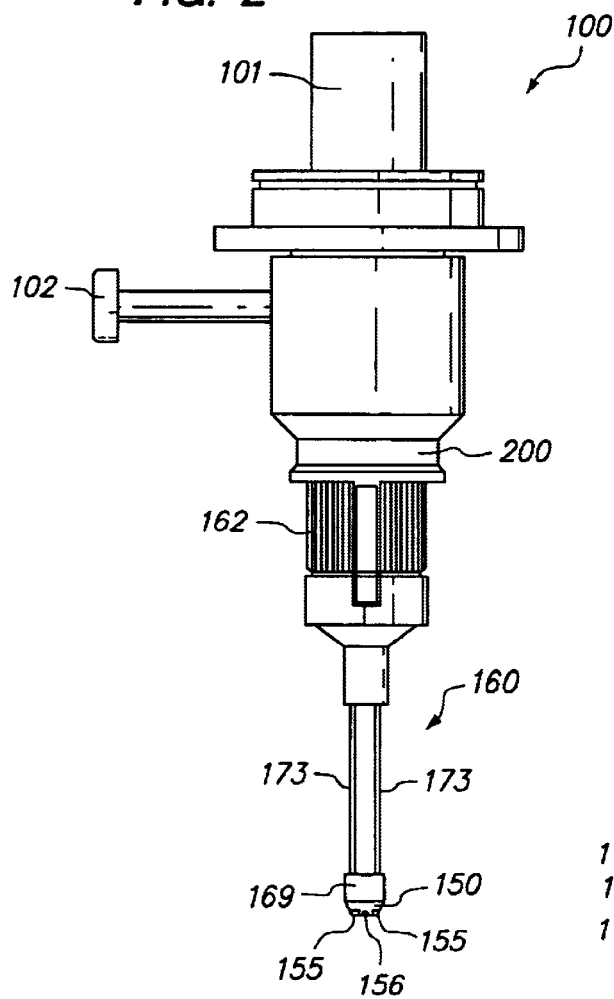
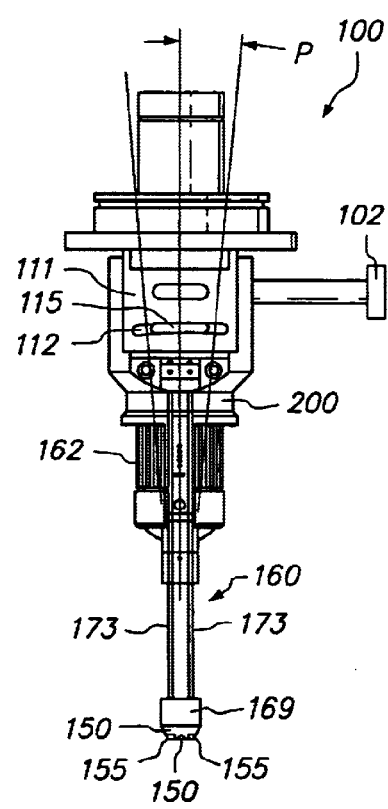

DEVICE AND METHODS OF INSPECTING SOLDERED CONNECTIONS

TECHNICAL FIELD

The present invention relates to devices and methods for inspecting soldered connections, more particularly the device of the present invention allows for visually inspecting concealed soldered connections such as those utilized to attach an integrated circuit to a printed circuit board.

BACKGROUND OF THE INVENTION

With the advances in technology related to integrated circuits (ICs) and in particular to surface mount IC's and more particular to ball grid arrays (BGAs) and chip scale packages (CSPS) and flip chips (FCs) in addition to the density of ICs utilized in electronics devices it has become increasingly difficult to visually inspect the integrity of the soldered connection between the chip leads and the solder pads on a printed circuit board. In addition, the number of soldered connections per chip has increased while inversely the size of the chip has decreased. While some surface mounted ICs have soldered connections which can be visually inspected because the chip leads project from the edge of the IC, the above-referenced chips cannot be visually inspected without an inspection device because the chip leads project perpendicular to the surface of the IC, and therefore the soldered connections are hidden by the IC.

One method to test the integrity of a soldered connection is that shown in U.S. Pat. No. 6,288,346 Hirofumi et al. wherein a plurality of test lands are disposed upon the circuit board which are connected to solder pads to which a BGA package is to be soldered to in which the continuity between the pins on the BGA can be confirmed. While this inspection method may disclose an open connection it cannot distinguish if there is a 'bridged-connection' that is where a ball of solder connects more than one pin. A bridged connection may lead to component failure when power is applied to the IC, therefore it is desirable to determine if bridged connections exist. Additionally, the testing method of Hirofumi et al. does not disclose the quality of the soldered connections, that is whether the solder was not heated to a high enough temperature. Therefore, the expected lifetime of the soldered connection cannot be estimated which may lead to more product failure after sales.

Another method to check soldered connections for the above-referenced IC's is through the use of x-rays. With x-ray inspection, it can be determined whether there are open connections, bridged connections and if the BGA was properly aligned with the solder pads of the printed circuit board. It is not possible to determine the quality of the soldered joint, as described above. In addition, it cannot be determined if excess flux residue remains within the soldered connections. Still further, the use of x-ray inspection requires dedicated equipment in addition to requiring protection from radiation exposure from the x-ray testing device. Lastly, x-ray inspection units require a skilled operator to utilize the device, thereby leading to complexity as well as costs to the overall product.

Still yet another method of inspection that is known is the production of a micrograph in cross-section through a soldered connection. This requires destructive testing, wherein a circuit board is taken from the assembly line and a cut is made passing through the IC to visually inspect the soldered connection. Though, this method will only produce an estimate of the actual soldered connections and requires that conclusions must be drawn as to the operating parameters of the soldering process.

Another known process of inspecting soldered connections is through the use of devices which can transmit images from one location to another, such devices include endoscopes and borescopes. These devices generally have a cylindrical profile and include a plurality of lenses disposed therein for the transmission of an image therethrough. A shortcoming of these devices is that at one end of the device there is disposed a light source adjacent to an image collection device. The light source is utilized to illuminate the area adjacent to the image collection device wherein an image is then reflected into the endoscope and transmitted to the opposite end. The clarity of the transmitted image may be diluted due to excess light emitted and/or reflected from the light source which is transmitted through the device.

Referring now to U.S. Patent Application Publication No. 2001/0024273 Cannon, there is disclosed yet another device for the inspection of soldered connections. In particular, the inspection device shown and described in the above-referenced patent application can be utilized to visually inspect soldered connections of BGA, CSPS, and FCs. The device includes an ocular unit, a lens head, and image transmission unit for transmitting the image receive by the lens head to the ocular unit and an illuminating device. As shown and described in Cannon the device therein may be utilized by placing the lens head adjacent to a BGA to be inspected. An illumination source illuminates the soldered connections while a second illumination source is utilized to backlight the soldered connections. A prism assembly disposed within the lens head receives a reflected image of the soldered connections, the reflected image is transmitted through an image transmission unit and into a camera. An aperture is disposed between the transmission unit and the camera to control the image received by the camera. A shortcoming of the device of Cannon is that the image reflected through the image transmission unit contains "interference" which leads to the degradation of the image. The term "interference" refers to the excess reflected light which will be transmitted through the image transmission unit. This excess light will combine with the image to be view, wherein the final combination of the image to be viewed and the interference will then be filtered by the aperture disposed adjacent the camera. An additional shortcoming of the device of Cannon is that the field of view of the lens head is to narrow to visually inspect both the upper solder connections as well as the lower solder connections, in order to visually inspect both, the lens head must be moved away from the soldered connections to provided a greater field of view, though at the cost of clarity of the image. A further shortcoming of the Cannon device is that a prism is utilized to reflect the image of the soldered connections, it is well known that prisms tend to be brittle and therefore require protection. For example, as shown in Cannon the prism is protected by webs, these webs extend beyond the edge of the prism, therefore the leading edge of the prism cannot be lowered such that the prism contacts the circuit board because of the protection webs. Lastly, prisms are very expensive therefore increasing the overall cost of the inspection device, as well as requiring specially trained technicians for repairs and/or servicing of the prism assembly.

Therefore there is a need for a device and methods of use which will enable the visual inspection of soldered connections, wherein the device provides a clear image of both the upper and lower connection without having to readjust the focal length of the device. Additionally, there is a need for an optical inspection device that eliminates interference within the transmitted image, thereby providing a better image of the soldered connection.

SUMMARY OF THE INVENTION

In accordance with the present invention there is provided a device for inspecting solder connections between a component and a substrate or between two components or substrates, the device includes an image receiving unit, an image transmitting device, including a first end and a second end, the first end coupled to the image receiving unit. A tip assembly removably coupled to the second end of the image transmitting device, the tip assembly further including a reflective device and an image receiving aperture, the tip assembly configured to transmit an image of the solder connections received by the reflective device, through the image transmitting device, to the image receiving unit, and an illumination device, including a light source, at least one light transmitting device, and at least one light emitting aperture disposed adjacent the image receiving aperture, the light emitting aperture directed towards the solder connections to be inspected.

In accordance with the present invention there is provided a device for optically inspecting soldered connections, the device including, a camera, and an image transmitting device. The image transmitting device including a generally circular cross-sectional profile first end and a second end and a bore extending therethrough, the first end coupled to the camera, and a at least one image transmitting lens disposed within the bore. A tip assembly removably coupled to the second end of the transmitting device. The tip assembly further including a mirror and an image receiving aperture disposed adjacent to the mirror, the image receiving aperture and the mirror configured to receive and transmit an image the soldered connections to the camera through the image transmitting device, and at least one illumination device, the illumination device comprising a light source, a device for transmitting light from the light source to a light transmitting aperture disposed within the tip assembly, the light transmitting aperture disposed adjacent to the image receiving aperture.

In accordance with the present invention there is provided a method of inspecting soldered connections between an IC and a circuit board, the method including the steps of disposing a circuit board having at least one IC soldered thereto on a work surface of an inspection device. Aligning a tip of the inspection device with a row of soldered connections to be inspected. Using an optical inspection device to view the soldered connections between the IC and the circuit board, the optical inspection device including a camera, an image transmitting device comprising a generally cylindrical member having a first and second end the first end coupled to said camera, and a removable tip assembly coupled to the second end of the image transmitting device, the removable tip assembly including a main body housing at least one light transmitting aperture and a reflective device and an image receiving aperture disposed adjacent to the light transmitting aperture, the light transmitting aperture and image receiving aperture directed toward the soldered connections to be inspected, the reflective device adapted to receive and transmit and image of the soldered connections to the camera. Illuminating the soldered connections to be inspected, and visually examining the soldered connections between the IC and the circuit board by pivoting the camera, image transmitting device, and tip assembly about an optical centerline of the reflective device to view the upper or lower solder connections and rotating the camera, image transmitting device, and the tip assembly through about 90 degrees to view the sides of the soldered connections. Moving the IC relative to the tip assembly to visually inspect other soldered connections between the IC and the circuit board, and visually inspecting the gaps formed between the soldered connections for optical clarity.

BRIEF DESCRIPTION OF THE DRAWINGS

In the drawings, wherein like numbers have be utilized to denote the same or similar parts:

FIG. 2. is a front view of the optical inspection unit of the inspection device according to an exemplary embodiment of the present invention;

FIG. 3. is a back view of the optical inspection unit of the inspection device according to an exemplary embodiment of the present invention illustrating the pivoting mechanism in accordance with the present invention;

DETAILED DESCRIPTION OF THE PREFERRED EMBODIMENT

The present invention comprises a test device for inspecting solder connections between a substrate and an integrated circuit. The test device includes a base assembly and an optical inspection unit connected to the base. The base further including a substantially horizontal work area wherein a component to be inspected in placed. The optical inspection unit may be moved vertically and rotatable with respect to the work area.

Figure 1:
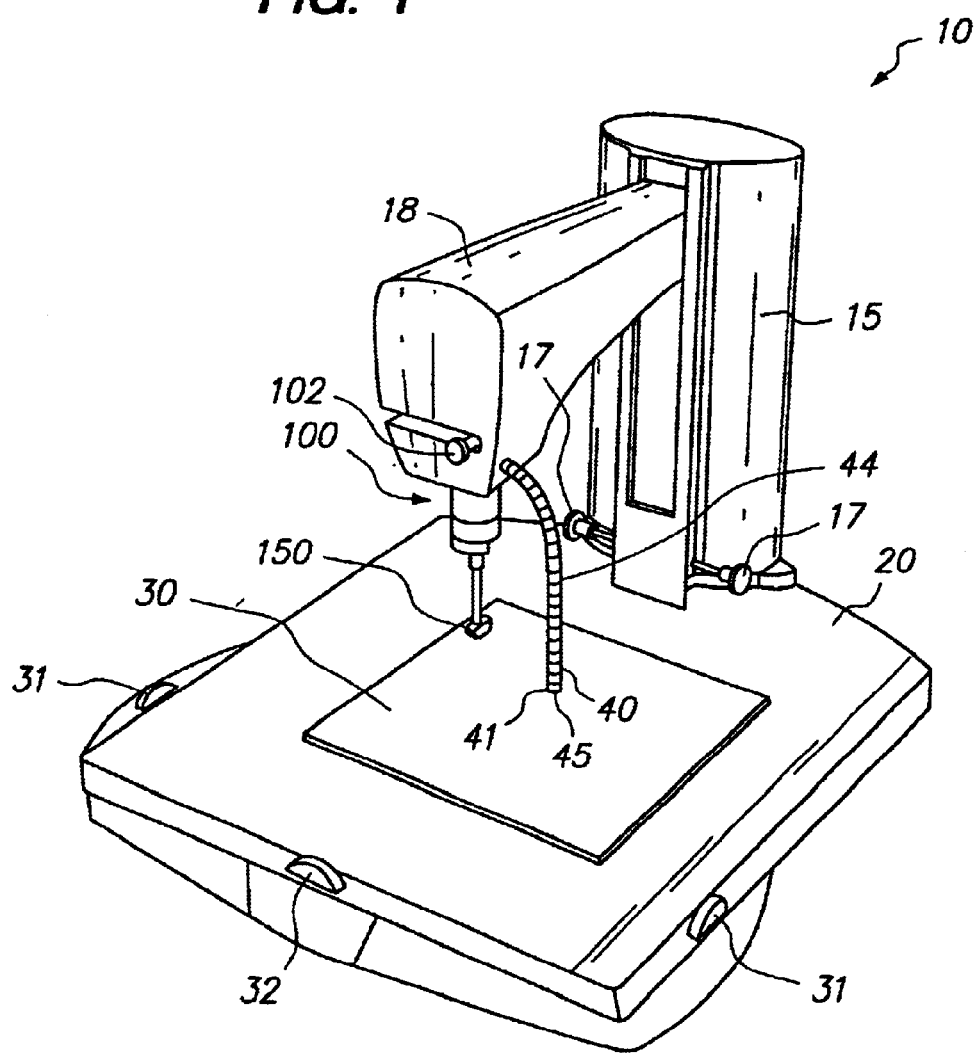
FIG. 1. is a perspective view of the inspection device according to the present invention.

Referring now to FIG. 1 there is shown the testing device 10 in accordance with the present invention. The testing device 10 includes a base assembly 20, and an optical inspection unit 100. The base assembly 20 further comprises a horizontal work surface 30, wherein the horizontal work surface 30 can be moved in both a vertical and horizontal plane relative to the optical inspection unit 100.

The work surface 30 may be displaced by rotating the knobs 31 and 32, the knobs 31 and 32 being operatively coupled to the work surface 30 utilizing known mechanical means. Alternatively, the work surface 30 may be coupled to an electrical drive system, wherein the knobs 31 and 32 control electrical switches which power drive motors coupled to the work surface.

As shown in FIG. 1, the base assembly 20 further includes a vertical member 15 fixedly attached thereto and protruding perpendicular to the work surface 30. The vertical member 15 is further configured to receive arm 18, wherein arm 18 may be coupled to vertical member 15 through a gear drive assembly, the gear drive assembly controlled by knobs 17 whereby the knobs 17 may be utilized to control the height of the arm 18 relative to the work surface 30. It shall be understood that the use of a gear driven assembly to control the height of arm 18 is merely exemplary and should not be considered limiting in any manner. It is contemplated that many different mechanical, electromechanical, electrical, and hydraulic systems may be utilized to control the height of arm 18 relative to the work surface 30. Additionally, the control means 17 may further include a locking means, thereby enabling a user to fix the height of the arm 18 relative to the work surface 30.

The arm 18 further includes receiving means adapted to receive an optical inspection unit 100 as shown in FIG. 1. Additionally, as shown, the testing device 10 may further include a second illumination device 40 configured to provide additional illumination to the soldered connections to be viewed. The second illumination device includes a tip 41, a flexible shaft 44, and a device for transmitting light 45. The device for transmitting light may include at least one LED disposed within the tip 41. Preferably, the device for transmitting light comprises a light pipe or fiber optic device, wherein one end is connected to a light source and the other end is configured to emit light from the tip 41, the tip 41 may further include a prism or mirror to reflect light in a desired direction. The light source may be the same source for use with the illumination device disposed within the tip assembly as will be described in detail below, or it may be a second source. Additionally, the second illumination device is configured to be moved independently of the movement of the inspection unit 100, thereby enabling a user to place the second illumination device at any desired position and height.

Referring now to FIG. 2, there is shown an exemplary embodiment of the optical inspection unit 100 in accordance with the present invention. As shown in FIG. 2, the optical inspection unit 100 comprises a coupling device 101, a rotating assembly 200, a focusing assembly 162, an image transmitting device 160 and a tip assembly 150.

The coupling device 101 is adapted to be received with the frame 18 wherein the coupling device retains the optical inspection unit 100 within the frame 18. The coupling may be fixedly received within the arm 18 or alternatively the coupling 101 may be rotatably received within the arm 18, thereby allowing the optical inspection unit 100 to be rotated relative to the arm 18 and the work surface 30.

The rotating assembly 200 includes the rotating knob 102 and a gear drive unit (not shown) and a pivot plate 111 as shown in FIG. 3. The pivot plate 111 further includes a groove 112 and a pin 115 disposed within the groove. Referring now to FIGS. 1, 2, and 3, it can be seen that rotating knob 102 projects from a groove formed within arm 18. Displacing the rotating knob 102 within the groove acts upon a gear drive assembly coupled to the camera, the focusing unit, the image transmitting device 160, and the tip assembly 150, thereby rotating the assembly clockwise and counterclockwise relative to an axis perpendicular to the work surface 30. In addition to the above, the optical inspection unit 100 may further be pivoted about the optical centerline of the reflective device disposed within the tip assembly. The optical inspection unit may be pivoted by rotating the rotating knob 102 clockwise or counter clockwise. The pivoting assembly can be better understood with reference to FIG. 3, where there is shown the pivot plate 111, the pivot plate including a groove 112 disposed therein and a pin 115 disposed within the groove 112. In use, the pivot plate 111 is fixedly attached to the coupling device 101 which is attached to the arm 18, thus allowing the optical inspection unit to pivot relative to the vertical support member 15. By pivoting the optical inspection unit 100 about the optical centerline of the reflective device disposed within the tip assembly allows for the inspection of both the top soldered connections as well as the bottom soldered connections without having to change the focal length of the reflective device relative to the soldered connections. The optical inspection unit pivots through on angle of P, the angle P can be between about 0 and about 180 degrees, preferably between about 0 and about 45 degrees, more preferably between about 0 and about 10 degrees, and most preferably between about 0 and about 5 degrees. It shall be understood that the assembly maybe pivoted about either side of an axis perpendicular to the work surface 30.

As shown in FIGS. 2 and 3 the optical inspection unit 100 includes a focusing device 162. The focusing device is operatively coupled to the camera 200 and the image transmission unit 160, wherein the focusing device 162 may further include a plurality of lenses, whereby the focal length of the lens may be adjusted by rotating the focusing assembly. Additionally, the focusing assembly may be utilized to adjust the sharpness of the image. It shall be understood that the focusing assembly as described herein and as utilized within the present invention does not include an aperture. The camera 200 may be a conventional film camera, more preferably the camera 200 is a digital camera such as a CCD camera or similar electronic cameras which provide a video output that may be displayed on a conventional display such as a cathode ray tube CRT device or a liquid crystal display LCD device.

Referring now FIGS. 2 and 3, there is shown an exemplary embodiment of the image transmission unit 160 in accordance with the present invention. The image transmission unit 160 comprises a generally cylindrical body having a first end and a second end, the first end being coupled to the focusing assembly 162, the second end being adapted to receive the tip assembly 150. The image transmission unit 160 may further include a plurality of lenses disposed therein. The generally cylindrical body may be constructed of a rigid material or of a flexible material. Additionally, as shown in FIGS. 1 and 2 a plurality of light transmitting elements 173 may be disposed upon the image transmission unit. The light transmitting elements may be fiber optic bundles, polished hollow cylindrical tubes, or other devices which may be utilized to transmit light. In a preferred embodiment the light transmitting elements are fiber optics which may comprise one or more elements. The light transmitting devices include a first end and a second end, the first end coupled to a light source (not shown) and the second end configured to be received within the tip assembly 150. The light source may comprise a conventional monofilament bulb, more preferably the light source is a metal halide lamp. Alternatively, it is contemplated that other sources of illumination may be utilized. In an alternative embodiment (not shown) it is contemplated that light emitting diodes (LED) may be disposed within the tip assembly 150 thereby eliminating the need for the light transmitting elements, wherein the light transmitting elements would be replaced with power cords for powering the LED's installed in the tip assembly.

Figure 4:
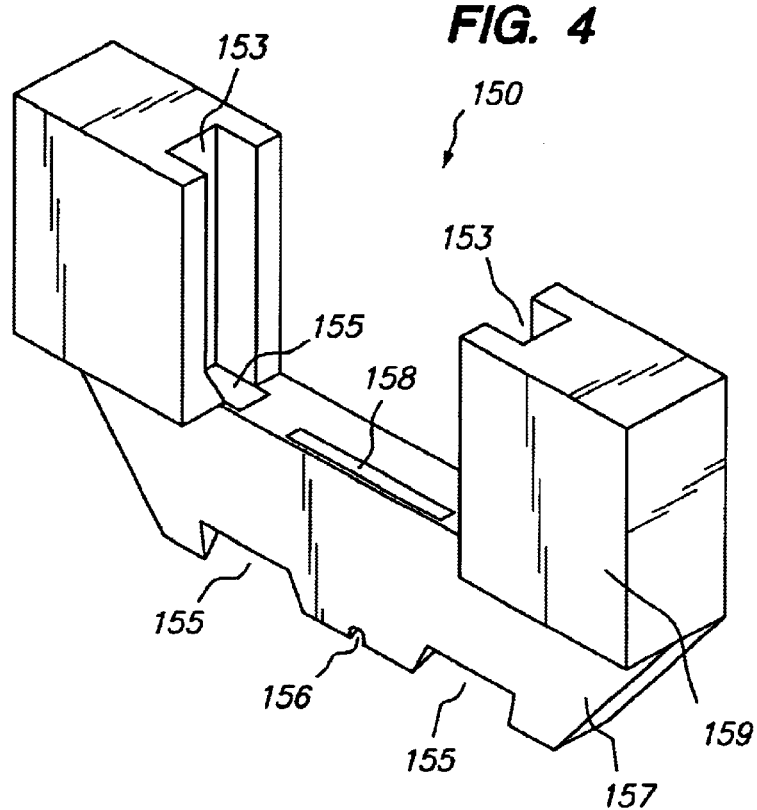
FIG. 4. is an isometric view of the tip assembly in accordance to an exemplary embodiment of the present invention.

Referring not to FIG. 4 there is shown a exemplary embodiment of the tip assembly 150 in accordance with the present invention. The tip assembly 150 includes a main body 159, at least one light transmitting aperture 155, a mirror, prism or similar reflective device, and an image receiving aperture 156 formed within the housing, wherein the image receiving aperture 156 is formed having a predetermined diameter which has been chosen to improve the quality of the image to be received by the camera. This is unlike conventional inspection devices wherein the aperture is placed adjacent to the camera assembly, by placing the aperture of the camera assembly before the reflective device reduces the amount of light pollution transmitted to the camera for magnification.

The main housing 159 may be formed of metal or plastic or any combination thereof. In a preferred embodiment, the main housing 159 is formed of plastic. The main housing 159 may be formed of multiple pieces which are assembled together, or alternatively, the main housing may be formed of a unitary body wherein the mirror or reflective element is has been molded therein.

Figure 6:
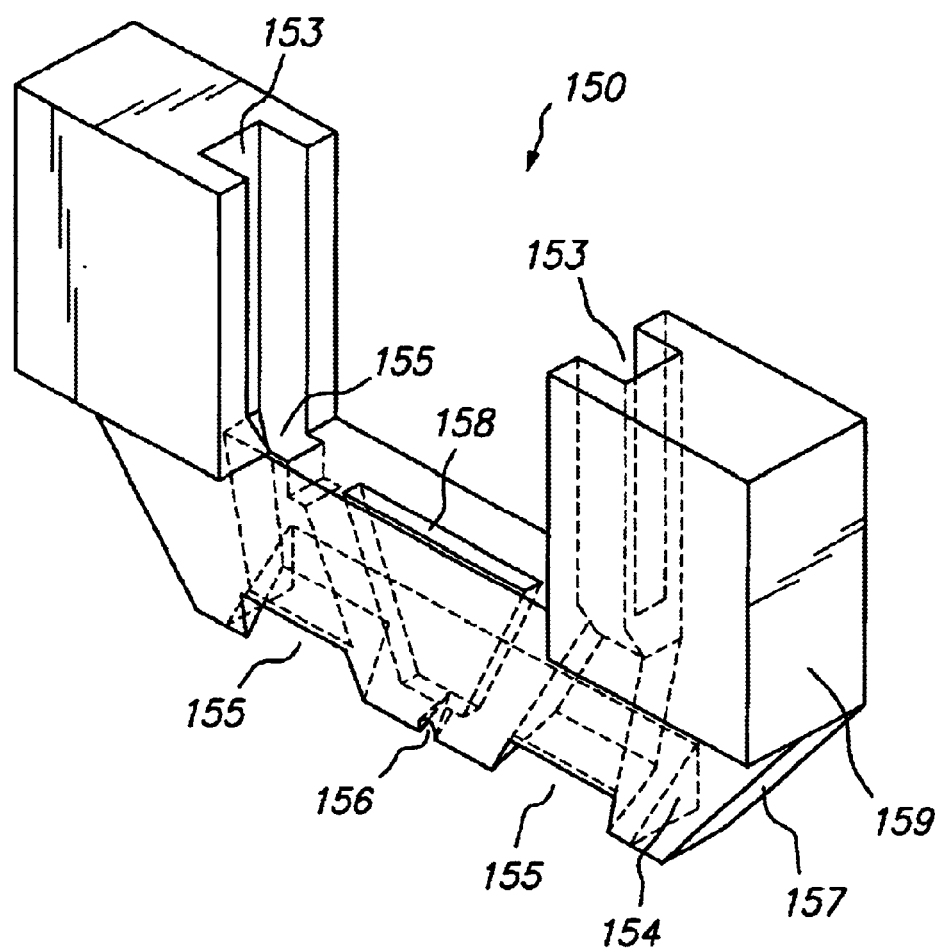
FIG. 6. is an isometric view of the tip assembly illustrating the mirror disposed within the tip assembly.

Referring now to FIG. 6, it can be seen that the reflective device 154 is disposed within the lower portion of the main housing 159 such that light transmitted through the apertures 153 will be reflected by the reflective device in the direction of the soldered connections to be viewed. Additionally, as shown in FIG. 6, it can be seen that the image receiving aperture 156 is disposed between the soldered connections to be viewed and the reflective device 154. By placing the image receiving aperture 156 between the soldered connection to be viewed and the reflective device 154 a sharper and clearer image is transmitted to the camera assembly for magnification as described in detail in another section of the current application.

Referring now to FIG. 4 it can be seen that the main body 159 further includes a reduced thickness region 157 as shown. The reduced thickness region 157 enables the tip assembly to be constructed having a lower profile, and therefore require less room between IC's installed on a circuit board. Furthermore, as shown in FIG. 6, the leading edge of the reflective device can be placed very near to the lower edge of the reduced thickness region 157, thereby enabling the reflective device to be placed closer to the work surface 30 or closer to a circuit board, thereby enabling lower profile assemblies to be inspected.

The main housing 159 further includes at least one light emitting aperture 155 formed therein, wherein the light emitting aperture is configured to utilize the reflective device to reflect light in the direction of the soldered connections to be viewed. In a preferred embodiment, the main housing includes two separate light emitting apertures 155 as shown in FIG. 4. The benefit of utilizing two separate light emitting apertures will become apparent following the discussion below regarding the image receiving aperture 156.

As described above, the tip assembly includes a image receiving aperture 156 disposed adjacent the distal end of the reduced thickness section 157. The image receiving aperture 156 is operatively coupled to the mirror and the image transmission aperture 158 formed within the main body 159 of the tip assembly. The image receiving aperture 156 replaces a conventional (camera) aperture which may be disposed within the lens assembly of the camera or within the camera body. Forming the image receiving aperture 156 into the tip assembly provides many benefits over conventional style inspection devices wherein the aperture is disposed adjacent the camera. A primary benefit that is provided, is that the image receiving aperture 156 acts as a filter to block excess light from the light source(s) from being transmitted to the camera.

In a conventional inspection device, because the aperture is mounted adjacent the camera, the reflected image as well as excess light from illumination sources is transmitted to the camera assembly, the excess light causes interference in the image quality and degrades the overall image. This degradation of the image means that either post-processing of the image must occur in order to clarify the image, or alternatively excessive magnification must be utilized to provide a clear image. Therefore, as described above the image receiving aperture 156 filters excessive light from the image to be viewed. Unlike a conventional optical aperture disposed within a camera lens or camera body, the image receiving aperture according to the present invention is formed having a pre-determined diameter, that is the image receiving aperture 156 is non-adjustable, unlike conventional photographic apertures. Though it is contemplated that an adjustable aperture could be fabricated wherein the tip assembly further includes a removable portion, wherein the removable portion includes the image receiving aperture, therefore to adjust the aperture size, removable portions could be substituted. Alternatively, the image receiving aperture 156 could be fabricated to comprise a conventional mechanical aperture.

Referring now to FIG. 6, there is shown a cross-sectional side view of the tip assembly according to the present invention. As shown in FIG. 6, the tip assembly 150, reflective device 154 is disposed within the reduced thickness section 157. As shown, the image receiving aperture 156 is disposed optically in front of the reflective device 154.

In addition to the advantages described above by placing the aperture on the tip assembly in the manner shown and described allows the use of a image transmitting unit 160 to extend the distance between the tip assembly and the camera assembly. This is not possible with other inspection devices that utilize a reflected image and an aperture mounted on a camera because the image degradation is to great over large distances as well as the increase in noise introduced to the image as described above.

Figure 5:
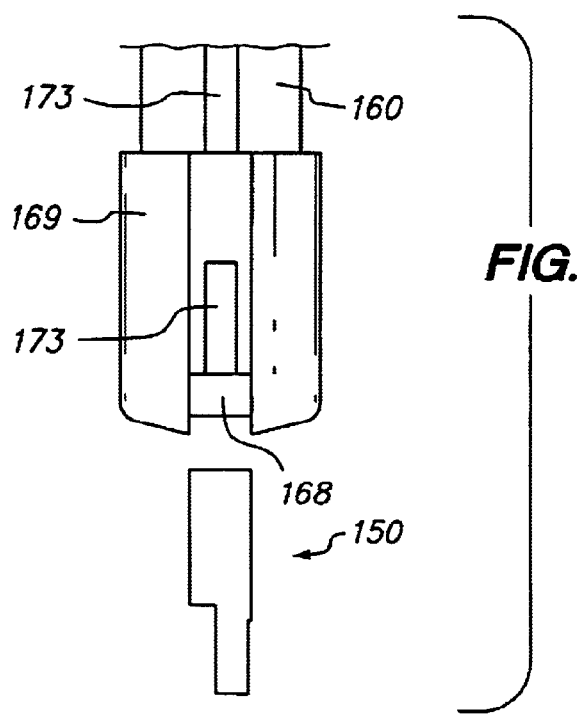
FIG. 5. is a partial side view of the tip assembly and tip assembly holder in accordance to an exemplary embodiment of the present invention.

Referring now to FIG. 5, there is shown the tip assembly 150 and the tip carrier 169. The tip carrier comprises a main body 170 disposed upon the first end of the image transmitting unit 160. The main body 170 of the tip carrier is configured to receive the light transmitting devices 173 disposed upon the image transmitting unit 160. Still further, the main body is further adapted to removably receive the tip assembly 150 as shown. Referring now to FIG. 4 it can be seen that the main body 150 of the tip assembly 150 is adapted to slidably receive the light transmitting devices within channels 153 formed in the main body. Additionally, as shown the channels 153 are separated from the image transmission aperture, thereby forming an enclosed optical path between the image transmitting aperture and the image receiving aperture 156.

It is contemplated that different tip assemblies could be fabricated which can be disposed within the tip carrier 169. That is tip assemblies having larger or smaller apertures to control the quality and/or size of the image. In addition, during an inspection process the tip may contact the integrated circuit being inspected. If this were to happen, many times the tip is damaged or destroyed, in a conventional inspection device this would require a skilled technician to perform service on the device. The present invention allows for anyone to easily replace the tip without requiring complex service steps. That is, the damaged tip could be removed from the first end of the image transmission device, discarded and then a new tip couple be slid and locked into place. This provides the benefit of not requiring a service call, and further reduces the down time of the inspection device due to repairs. Another improvement of the present invention over conventional inspection devices is that if the mirror disposed within the tip assembly becomes dirty due to contamination or for any other reason it may be easily and inexpensively replaced.

Referring now to FIGS. 1–6 the use of the inspection device according to the present invention will be described. In use, a circuit board containing at least one IC having been soldered thereto is placed within the work surface 30. The inspection device 100 is moved into position such that the image receiving aperture 156 is disposed to view the soldered connections of the IC. It is contemplated that the work surface 30 may be moved relative to the inspection device 100 or the circuit board may be moved or further still the inspection device 100 may be moved or any combination of the above may be moved. After the image receiving aperture 156 is disposed within a position to view the soldered connections an image is displayed on a display device (not shown) such as a monitor, LCD panel, television, or similar devices. After, viewing the soldered connections, the rotating knob may be rotated clockwise or counterclockwise to pivot the inspection device 100. By pivoting the inspection device this will allow the image receiving aperture to receive an image of either the top soldered connections or the bottom soldered connections without requiring the inspection unit to be moved relative to the IC to be inspected, unlike conventional inspection devices which must be moved away from the IC in order to expand the field of view which results in a loss of image clarity. After the upper and lower soldered connections have been viewed, the rotating knob may be rotated within the groove disposed in the arm 18, thereby directing the image receiving aperture 156 to view other rows of soldered connections or to view the soldered connections at a different angle. Throughout the procedure described above, light is emitted from the apertures 155 of the tip assembly to illuminate the soldered connections to be viewed. Additionally, the second illumination device may be disposed on the side opposite to the tip assembly to provide backlighting of the soldered connections, or in any other position to provided desired lighting. As shown in FIG. 1, the second illumination source, in a preferred embodiment, may be moved independently relative to the tip assembly 150, though it is contemplated that the second light source may be coupled to the movement of the imaging device 100 such that less user intervention is needed to provide the necessary lighting. By providing a second illumination device which may be moved independent of the imaging device 100 allows the inspection device 10 according to the present invention to be utilized to inspect ICs that may have heat sinks or similar devices coupled thereto because the inspection device 100 and the second illumination device 40 may be moved independently about the IC to be inspected.

It shall be understood that the examples described herein and shown in the appended figures are exemplary and should not be considered limiting in any manner. It is contemplated that one skilled in the art may undertake modifications to the present invention without deviating from the scope of the invention.

What is claimed is:

1. A device for inspecting solder connections between a component and a substrate or between two components or substrates, the device comprising:
    an image receiving unit;
    an image transmitting device, including a first end and a second end, the first end coupled to said image receiving unit;
    a tip assembly removably coupled to said second end of said image transmitting device, said tip assembly further including a reflective device and an image receiving aperture, the tip assembly configured to transmit an image of said solder connections received by said reflective device, through said image transmitting device, to said image receiving unit; and
    an illumination device including at least one light emitting aperture disposed adjacent said image receiving aperture, said light emitting aperture directed towards said solder connections to be inspected.

2. The device according to claim 1, wherein the image receiving unit comprises a camera.

3. The device according to claim 2, wherein the image transmitting device includes a generally cylindrical body having a plurality of lenses disposed therein.

4. The device according to claim 1, wherein the image receiving unit includes a lens assembly coupled thereto, said lens assembly capable of increasing or decreasing magnification of said image to be received therein.

5. The device according to claim 1, wherein said illumination device includes light source and a device for transmitting light from the light source to the light emitting aperture.

6. The device according to claim 1, wherein said image receiving unit is disposed within a housing, said housing pivotally attached to a frame.

7. The device according to claim 6, wherein a pivot point of rotation of said housing is the optical centerline of said mirror disposed within the tip assembly.

8. The device according to claim 7, wherein said image transmitting device and said tip assembly are rotatable about an axis perpendicular to said substrate.

9. The device according to claim 1, wherein said aperture filters the image to be transmitted prior to transmission of the image by the image transmitting device.

10. The device according to claim 1, further including a display device coupled to said image receiving unit, the display device configured to display the solder connections to be inspected.

11. The device according to claim 1, wherein said tip assembly further includes an illumination aperture disposed on either side of said image receiving aperture, wherein said illumination apertures direct light onto said solder connections to be inspected.

12. The device according to claim 6, wherein said angle of pivot is between about 0 and about 5 degrees.

13. The device according to claim 1, further including a back lighting assembly, the back lighting including an illumination source, a lens assembly, and a flexible arm coupled thereto.

14. The device according to claim 5, wherein said device for transmitting light is a fiber optic device.

15. The device according to claim 1, wherein the illumination device includes a light emitting diode disposed within said light emitting aperture and a power source coupled to said light emitting diode.

16. A device for optically inspecting soldered connections, the device comprising:
    a camera;
    a image transmitting device, including a generally circular cross-sectional profile first end and a second end and a bore extending therethrough, said first end coupled to the camera, and a at least one image transmitting lens disposed within the bore;
    a tip assembly removably coupled to said second end of said transmitting device, said tip assembly further including a mirror and an image receiving aperture disposed adjacent to said mirror, said image receiving aperture and said mirror configured to receive and transmit an image the soldered connections to said camera through said image transmitting device; and
    at least one illumination device, the illumination device comprising a light source, a device for transmitting light from the light source to a light transmitting aperture disposed within said tip assembly, the light transmitting aperture disposed adjacent to the image receiving aperture.

17. The device according to claim 16, further including a magnifying lens disposed between the camera and the first end of the image transmitting device, the magnifying lens capable if magnifying the image of the soldered connection.

18. The device according to claim 16, wherein said camera, image transmitting device, and tip assembly are rotatably and pivotally coupled to a movable arm, the movable arm coupled to a frame, the frame including a work surface configured to receive a circuit board to be inspected, the camera, image transmitting device and tip assembly being disposed generally perpendicular to said work surface.

19. The device according to claim 18, wherein the camera, image transmitting device, and tip assembly are pivotable between about −10 and about 10 degrees relative to an axis extending perpendicular from said work surface.

20. The device according to claim 19, wherein the camera, image transmitting device, and tip assembly may be rotated about said perpendicular axis.

21. The device according to claim 20, further including a second illumination device, the second illumination device comprising a flexible shaft extending from said arm and a tip assembly, the tip assembly including a light transmitting aperture, wherein a light transmitting device is connected at one end to a light source and at the other end to the light transmitting aperture, the second illumination device configured to move independent of said camera, image transmitting device, and said tip assembly.

22. A method of inspecting soldered connections between an IC and a circuit board, the method comprising:

a disposing a circuit board having at least one IC soldered thereto on a work surface of an inspection device;

aligning a tip of the inspection device with a row of soldered connections to be inspected;

illuminating the soldered connections to be inspected through a light emitting aperture disposed upon the tip of the inspection device;

visually examining the soldered connections between the IC and the circuit board through an image receiving aperture disposed upon the tip of the inspection device;

pivoting the tip assembly about an optical centerline of a reflective device disposed within the tip assembly to view the upper or lower solder connections;

rotating said tip assembly through about 180 degrees to view the sides of the soldered connections; and visually inspecting the gaps formed between the soldered connections for optical clarity.

23. The method according to claim 22, wherein the step of illuminating further comprises using a second illuminating device to illuminate the soldered connections from a direction opposite to the image receiving aperture.

* * * * *